United States Patent
Deane et al.

(10) Patent No.: US 9,327,048 B2
(45) Date of Patent: *May 3, 2016

(54) AIR TREATMENT DEVICE HAVING A PLASMA COIL ELECTROSTATIC PRECIPITATOR ASSEMBLY

(71) Applicant: Novaerus Patents Limited, Co. Dublin (IE)

(72) Inventors: Graham Deane, Dublin (IE); Kevin Maughan, Dublin (IE); Felipe Soberon, Dublin (IE); Niall O'Connor, Dublin (IE)

(73) Assignee: Novaerus Patents Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/806,723

(22) Filed: Jul. 23, 2015

(65) Prior Publication Data

US 2016/0015850 A1    Jan. 21, 2016

Related U.S. Application Data

(63) Continuation of application No. 14/724,151, filed on May 28, 2015.

(30) Foreign Application Priority Data

May 30, 2014  (GB) .................................. 1409674.7

(51) Int. Cl.
*A61L 9/22* (2006.01)
*B03C 3/45* (2006.01)
(Continued)

(52) U.S. Cl.
CPC . *A61L 9/22* (2013.01); *B01D 53/32* (2013.01); *B03C 3/017* (2013.01); *B03C 3/12* (2013.01);
(Continued)

(58) Field of Classification Search
CPC combination set(s) only.
See application file for complete search history.

(56) References Cited

U.S. PATENT DOCUMENTS 6,893,618 B2 * 5/2005 Kotlyar ...................... A61L 9/22
422/186.04
7,192,553 B2 * 3/2007 Crowe ........................ A61L 2/14
422/22

(Continued)

FOREIGN PATENT DOCUMENTS

EP    1285698    2/2003
EP    1433515    6/2004
(Continued)

OTHER PUBLICATIONS

PCT Search Report.
(Continued)

*Primary Examiner* — Duane Smith
*Assistant Examiner* — Sonji Turner
(74) *Attorney, Agent, or Firm* — Stephen T. Scherrer; Monique A. Morneault; Scherrer Patent & Trademark Law, P.C.

(57) ABSTRACT

An air treatment device having a plasma generator electrostatic precipitator assembly, is provided. The assembly includes an electrostatic precipitator configured to charge airborne particles in the vicinity of the electrostatic precipitator to provide charged airborne particles, and a plasma generator positioned in proximity to the electrostatic precipitator and configured for cooperation with the electrostatic precipitator. The plasma generator is configured to discharge plasma and provide an inactivation zone in the region of the plasma generator operable to inactivate airborne particles. The air treatment device directs the charged airborne particles generated by the electrostatic precipitator into the inactivation zone such that the air treatment device is adapted to generate charged airborne particles and then immediately, to direct the charged airborne particles into the inactivation zone so as to expose the charged airborne particles to plasma in the inactivation zone.

28 Claims, 16 Drawing Sheets

(51) Int. Cl.
  *B03C 3/70* (2006.01)
  *B03C 3/82* (2006.01)
  *B03C 3/41* (2006.01)
  *B01D 53/32* (2006.01)
  *B03C 3/017* (2006.01)
  *B03C 3/12* (2006.01)
  *B03C 3/49* (2006.01)
  *B03C 3/86* (2006.01)
  *H05H 1/24* (2006.01)

(52) U.S. Cl.
  CPC ... *B03C 3/41* (2013.01); *B03C 3/45* (2013.01); *B03C 3/49* (2013.01); *B03C 3/70* (2013.01); *B03C 3/82* (2013.01); *B03C 3/86* (2013.01); *H05H 1/2406* (2013.01); *B03C 2201/04* (2013.01); *B03C 2201/06* (2013.01); *B03C 2201/10* (2013.01); *H05H 2001/2412* (2013.01); *H05H 2001/2431* (2013.01); *H05H 2001/2462* (2013.01); *H05H 2240/10* (2013.01)

(56) References Cited

U.S. PATENT DOCUMENTS

| | | | | |
|---|---|---|---|---|
| 7,279,028 B2* | 10/2007 | Bergeron | | A61L 9/205 55/518 |
| 7,449,053 B2* | 11/2008 | Hallam | | A61L 9/015 95/58 |
| 7,452,410 B2* | 11/2008 | Bergeron | | A61L 9/205 95/57 |
| 7,559,976 B2* | 7/2009 | Krigmont | | B03C 3/08 55/DIG. 38 |
| 8,361,402 B2* | 1/2013 | Tsui | | A61L 9/22 422/186.07 |
| 8,673,068 B2* | 3/2014 | Volodin | | A61L 9/22 55/DIG. 38 |
| 2003/0007910 A1 | 1/2003 | Diamant Lazarovich et al. | | |
| 2003/0132100 A1* | 7/2003 | Crowe | | A61L 2/14 204/164 |
| 2004/0331476 | 2/2004 | Lee | | |
| 2004/0052700 A1* | 3/2004 | Kotlyar | | A61L 9/22 422/186.04 |
| 2004/0184972 A1* | 9/2004 | Kelly | | A61L 9/22 422/186.04 |
| 2007/0020159 A1* | 1/2007 | Tsui | | A61L 9/22 422/186.04 |
| 2008/0283411 A1* | 11/2008 | Eastman | | C10G 2/30 205/343 |
| 2009/0274592 A1* | 11/2009 | Bergeron | | B03C 3/09 422/186.29 |
| 2010/0072055 A1 | 3/2010 | Tanaka et al. | | |
| 2010/0168499 A1* | 7/2010 | Gutsol | | A61L 9/22 588/311 |

FOREIGN PATENT DOCUMENTS

| | | | |
|---|---|---|---|
| EP | 1666152 | 6/2006 | |
| EP | 1715553 | 10/2006 | |
| EP | 2581925 | 4/2013 | |
| GB | 2468865 | 9/2010 | |
| GB | 2496888 | 5/2013 | |
| JP | 2002143634 | 5/2002 | |
| JP | WO 2008062554 A1 * | 5/2008 | ............ B01D 53/32 |
| JP | EP 2085582 A1 * | 8/2009 | ............ B01D 53/32 |
| JP | 2012170869 | 9/2012 | |
| WO | 2004047877 | 6/2004 | |
| WO | 2011149188 | 12/2011 | |
| WO | 2013065205 | 5/2013 | |

OTHER PUBLICATIONS

Search report from corresponding priority UK application.

* cited by examiner

```
┌─────────────────────┐
│  Draw air flow with │ ─── 901
│      impeller       │
└─────────────────────┘
           │
           ▼
┌─────────────────────┐
│  Air flows through  │
│  electrostatic wire │ ─── 902
│     electrode 303   │
└─────────────────────┘
           │
           ▼
┌─────────────────────┐
│ Airborne particles in the │
│ air flow collect charge   │ ─── 903
│    from electrode 303     │
└─────────────────────┘
           │
           ▼
┌─────────────────────┐
│   Charged airborne  │
│  particles are forced│ ─── 904
│ towards the vicinity of│
│       coil 101      │
└─────────────────────┘
           │
           ▼
┌─────────────────────┐
│   Charged airborne  │
│ particles are collected│ ─── 905
│  by outer wire mesh │
│     electrode 602   │
└─────────────────────┘
           │
           ▼
┌─────────────────────┐
│ Pathogens present in│
│  collected airborne │
│ particles are exposed to│ ─── 906
│   plasma discharge and│
│      inactivated    │
└─────────────────────┘
```

AIR TREATMENT DEVICE HAVING A PLASMA COIL ELECTROSTATIC PRECIPITATOR ASSEMBLY

FIELD OF THE INVENTION

The present invention relates to an air treatment method and device. More specifically, the invention relates to an air treatment device comprising a plasma coil electrostatic precipitator assembly for air disinfection and pollution control.

The plasma generator electrostatic precipitator assembly preferably comprises a plasma coil electrostatic assembly and can be used for capturing airborne particles and inactivating pathogens and pollutants present in the particles. An atmospheric plasma discharge is used for providing an inactivation zone in which the pathogens and pollutants are inactivated.

BACKGROUND OF THE INVENTION

Health threatening airborne pollutants may be subdivided into three groups; (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air. The last category includes many cleaning chemicals, hair spray, various types of primer, and fuels such as gasoline and kerosene, as well as other household, beauty, or hobby products. Some fabrics, particularly those recently manufactured, also contribute to indoor airborne VOCs when they outgas, or leak out chemicals in gaseous form, over time.

Airborne pollutants can build up significantly in indoor environments with the result that the air that we breathe may become contaminated. Considering that on average humans spend approximately 90% of their time in an indoor environment, it will be appreciated that the removal of pollutants from indoor air is of importance to reduce allergies and prevent infection transmission, such as sick building syndrome.

Existing state of the art technologies for the control of airborne pathogens can be categorized as: (a) airborne trapping systems or filters, (b) airborne inactivation systems and, (c) some combination of the above.

Existing airborne inactivation technologies also include those that make use of chemicals, UV radiation and plasma discharge by-products.

Examples of chemical inactivation include the use of anti-microbial vaporizers, typically ozone or hydrogen peroxide. While these systems are effective, they are also disruptive, requiring the evacuation of indoor space to be treated and therefore are not suitable for use under normal living circumstances.

Alternative systems for the purification of air include using ultra violet light (UV) emission to kill airborne bacteria. For example, international publication No. WO 03/092751 describes a device in which a fluid (e.g. air) is passed through an array of UV lamps. In this solution the one and only inactivation mechanism is via UV radiation.

Prior art also includes the use of plasma radicals for sterilisation of air filter medium; see for example US publication No. 2004/0184972. In this document, it is proposed that an upstream plasma discharge can generate active radicals which flow upstream to a medium filter and kill any bacteria or virus trapped by the filter. However, the use of a filter medium to capture pathogens may still act as an infection reservoir and may also affect air flow stream as it gets clogged.

It is also known to use a plasma discharge which releases anti-pathogenic agents which inactivate pathogens in the air. Prior art includes methods and apparatuses for air treatment using a plasma discharge in which air is drawn around an electrode coil assembly. The plasma discharge inactivates any airborne pathogens flowing in the vicinity of the discharge. It is appreciated that the efficacy of such a device depends on the time period the pathogens and airborne pollutants are exposed to the plasma discharge and the anti-pathogenic agents generated by said device.

SUMMARY

Accordingly, a first embodiment of the present invention provides an air treatment apparatus in accordance with appended claim 1. Advantageous embodiments are provided in the dependent claims. The application also provides other aspects which are set out in an air treatment apparatus as detailed in claims 34, 35 and 40. Other features will be apparent from the description.

In one aspect, the present invention provides air treatment apparatus comprising: an electrostatic precipitator configured to charge airborne particles in the vicinity of the electrostatic precipitator to provide charged airborne particles; and a plasma generator positioned in proximity to but at a pre-determined distance from the electrostatic precipitator and configured for cooperation with the electrostatic precipitator, the plasma generator configured to create an inactivation zone in the region of the plasma generator; and wherein the air treatment device comprises means for directing the charged airborne particles generated by the electrostatic precipitator into the inactivation zone such that the air treatment device is adapted to generate charged airborne particles and then immediately, to direct the charged airborne particles into the inactivation zone so as to expose the charged airborne particles to plasma in the inactivation zone.

The means for directing the charged airborne particles generated by the electrostatic precipitator into the inactivation zone may comprise a voltage applied between the electrostatic precipitator and the plasma generator such that the air treatment device is adapted to generate charged airborne particles and, at the same time, to direct the generated charged particles, by attracting said charged airborne particles towards the plasma generator, into the inactivation zone so as to expose the charged airborne particles to plasma in the inactivation zone.

The inactivation zone is a zone in which plasma is released and is effective to inactivate airborne pollutant material including pathogens. Such airborne pollutant material (i.e. airborne pollutants), which can be health threatening, may be subdivided into three groups: (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air. The plasma generated by the plasma generator in the air treatment apparatus of the present invention is effective to inactivate any of the airborne pollutant materials as defined in subdivisions (a) to (c).

Thus, the air treatment apparatus is configured to attract the charged airborne particles into the inactivation zone; this is not the same as trying to attract all the charged particles onto the surface of the plasma generator as in fact, such would be undesirable as it could interfere with the effective operation of the plasma generator if all the charged particles were on the surface of the plasma generator.

The air treatment apparatus of the present invention comprises a plasma generator, preferably a plasma coil assembly, which is configured to operate at a power density less than 1 W/cm2 to operably generate a plasma discharge.

In the preferred embodiment, the plasma generator is a coil assembly, most preferably, a generally cylindrical coil assembly, which is configured to operate at a power density less than 1 W/cm2 to operably generate a plasma discharge circumferentially about a longitudinal axis of the coil assembly.

Most preferably, the plasma generator is configured to be operated at a power density in the range from 0.1 to 0.5 W/cm2. This is a relatively low power density for plasma generation and is effective for creating an inactivation zone about the plasma generator. This low power density of operation of the plasma generator of the present invention is in complete contrast to the relatively high level of power density that is required for conventional use of plasma generators for purification of exhaust gases such as in the automotive industry.

BRIEF DESCRIPTION OF THE DRAWINGS

The present application will now be described with reference to the accompanying drawings in which:

FIG. 11 is a flow chart diagram of the pathogen inactivation method in accordance with the present teachings;

DETAILED DESCRIPTION

Figure 1:
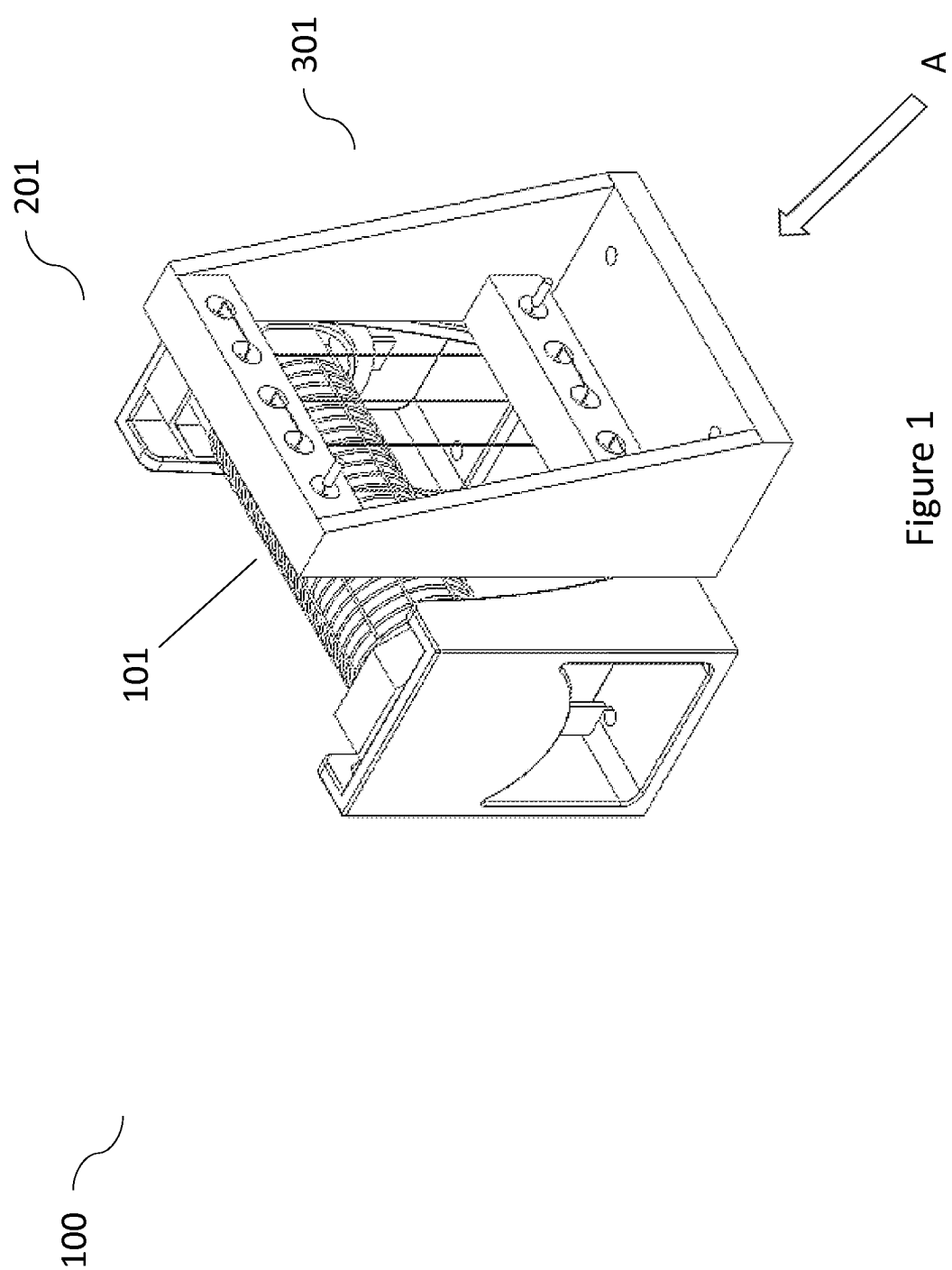
FIG. 1 is a perspective view of the plasma coil electrostatic precipitator assembly in accordance with the present teachings.
Figure 2:
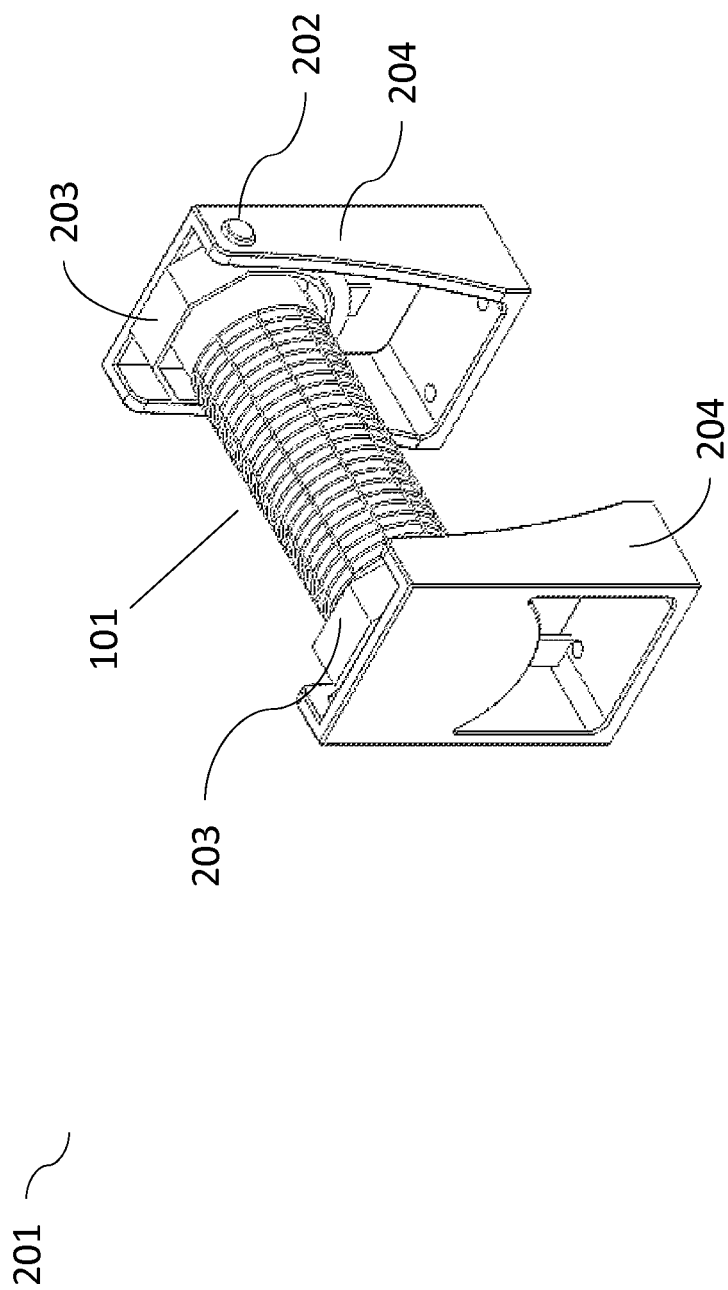
FIG. 2 is a perspective view of the coil assembly of FIG. 1.
Figure 3:
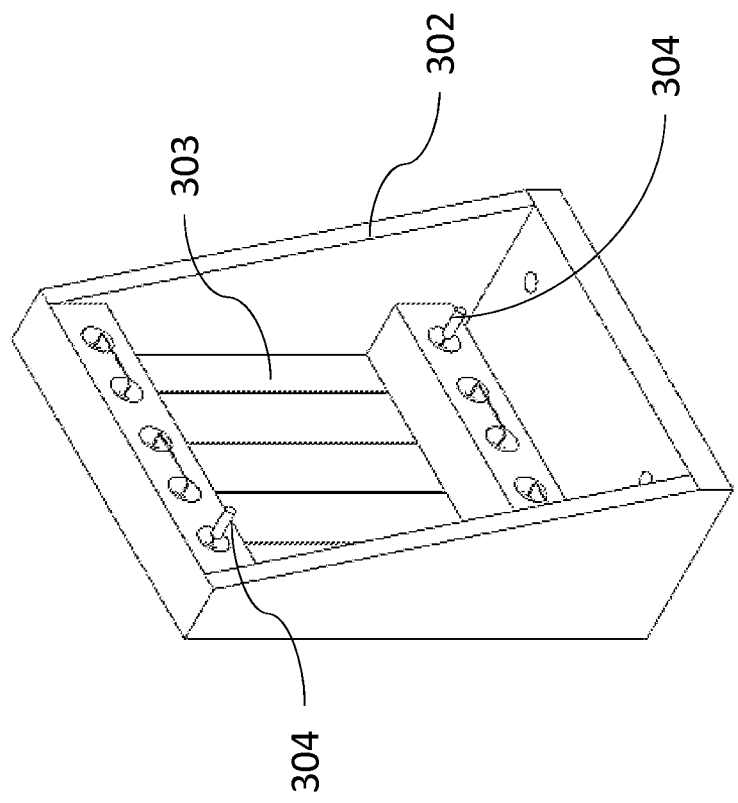
FIG. 3 is a perspective view of the electrostatic wire electrode assembly of FIG. 1.

The present teaching is based on an understanding by the inventors that the efficacy of treatment of airborne pathogens can be improved by combining a plasma discharge apparatus with an electrostatic precipitator. While electrostatic precipitators are known, heretofore they have been used exclusively as highly efficient filtration devices that remove fine particles, like dust and smoke, from a flowing gas using the force of an induced electrostatic charge minimally impeding the flow of gases through the unit. The present inventors have realised that by using functionality provided by an electrostatic precipitator in combination with a plasma generator that it is possible to improve the efficiency of treatment of airborne pathogens. A synergistic effect is provided by an apparatus that combines functions of two known techniques that heretofore have not been considered usefully employed together or compatible.

Known electrostatic precipitators consist of two sets of electrodes, the first with very thin and sharp edges is typically biased negatively with respect to a second electrode or plate of larger area. The negative, sharp, electrode supplies electrons to nearby airborne particles, charging them negatively. The positive plates or electrodes attract electrostatically and collect the charged particles, thereby removing them from the air. For example, see US publication No. 2013/0233172 which discloses an air cleaner with a built in electrostatic precipitator.

It is appreciated that electrostatic precipitators are efficient at airborne particle removal. However, these devices do not inactivate pathogens captured by their electrodes. It is to be noted that some pathogens may survive in unfavourable conditions for periods of time up to months; for instance in the case of spores. Such pathogens may lead to disease transmission as over time, some of the captured particles may be released back into the environment.

The present inventors have realised that by combining an electrostatic precipitator with a plasma discharge generator that it possible to effectively trap and destroy pathogens in a fashion which was not previously considered possible. The present teaching will now be described with reference to a number of embodiments of exemplary plasma coil electrostatic precipitator assemblies. It will be understood that these exemplary assemblies are provided to assist in an understanding of the present teaching and are not to be construed as limiting in any fashion. Furthermore, elements or components that are described with reference to any one figure may be interchanged with those of other figures without departing from the spirit and scope of the present invention. It will be appreciated that for simplicity and clarity of illustration, where considered appropriate, reference numerals may be repeated among the figures to indicate corresponding or analogous elements.

The plasma coil electrostatic precipitator assembly in accordance with the present teachings captures airborne contaminants and generates a plasma discharge field to effectively sterilise said air contaminants, including micro-organisms or pathogens or to oxidise organic airborne material and particles.

Figure 4:
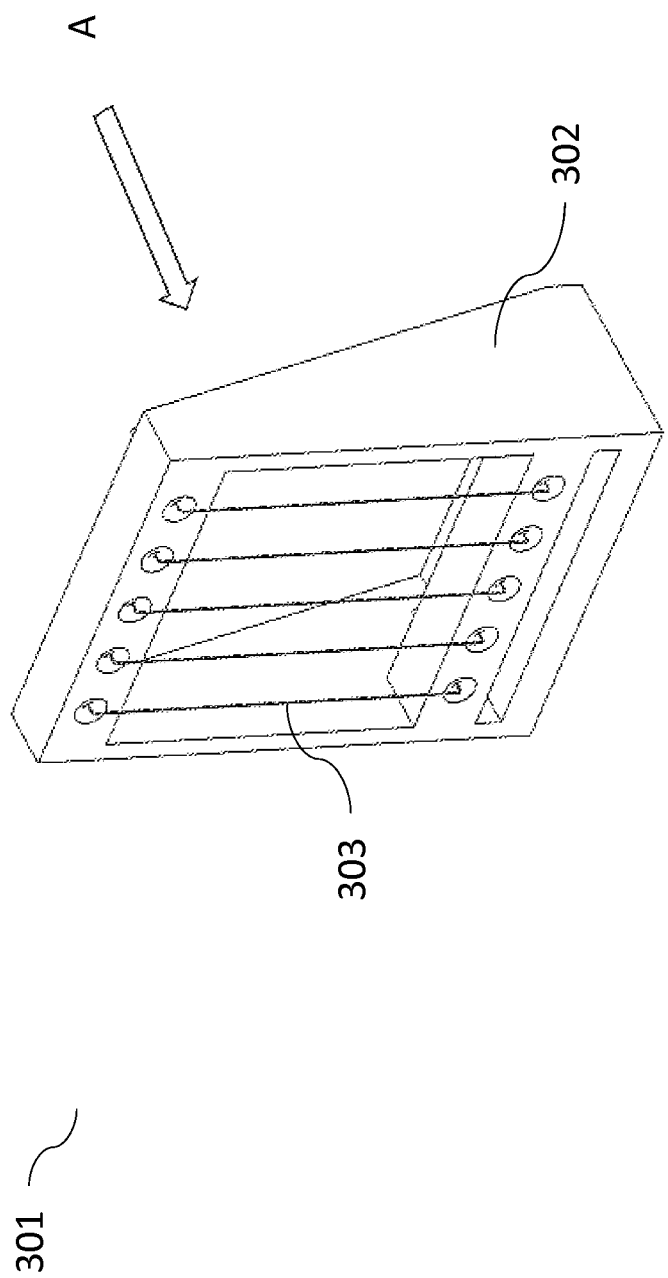
FIG. 4 is a different view of the electrostatic wire electrode assembly of FIG. 3.

The configuration of the plasma coil electrostatic precipitator assembly 100 is described with reference to FIG. 1, which shows a first embodiment in accordance with the present invention. A plasma coil assembly 201 is shown adjacent an electrostatic wire electrode assembly 301. As will be explained in more detail hereinafter, air is forced to flow, in the direction of arrow A shown in FIGS. 1 and 4, through the electrode assembly 301 and past the plasma coil assembly 201. It is to be noted that the air flow is over and under the plasma coil assembly 201; it is important to note that the air flow is not through the plasma coil assembly 201. The electrostatic wire electrode assembly 301 places a charge on airborne particles in the air flow. The charged particles are attracted to the coil 101 of the plasma coil assembly 201 and are collected on the coil 101. The coil 101 is configured to discharge plasma. Pathogens present in the charged particles collected on the coil 101 are exposed to this plasma discharge and are thereby inactivated.

FIG. 2 is a perspective view of the coil assembly 201 of FIG. 1, shown without the electrostatic wire electrode assembly 301, for the purpose of clarity of explanation. It can be appreciated that the coil 101 is supported and held, in a position that enables air flow above and underneath the coil 101, by insulating stands 204, one insulating stand 204 being provided at each end of the longitudinal axis of the coil 101. Dielectric retainers 202 are used to secure the cylindrical coil 101 in place on the insulating stands 204. Dielectric insulator caps 203 are also provided at each end of the cylindrical coil 101 to further insulate the coil 101 from the insulated stands 204. The combination of insulator caps 203 and insulated stands 204 ensures that the cylindrical coil 101 is insulated from any surface that the coil assembly 201 may be mounted upon. The insulator caps 203 have a further function in that they hold the various cylindrical elements of the cylindrical coil 101 together as will be further described hereinafter.

FIG. 3 shows the electrostatic wire electrode assembly 301 of FIG. 1 without the coil assembly 201, again for clarity of explanation. An insulating support 302 holds a wire electrode 303. The electrode 303 includes a single wire looped and oriented in the vertical direction. Electrical contacts 304 are attached to each end of the wire and terminate the wire electrode 303. These contacts 304 provide suitable electrical connections for a power supply (not shown). The power supply provides power to the wire electrode 303 which operably provides an electrical charge surrounding the electrode 303. The wire electrode 303 may be considered a discharge electrode as it emits charging current and provides voltage that generates an electrical field between the wire electrode 303 and the cylindrical coil 101. The electrical field forces particles in the air to migrate toward the plasma generator cylindrical coil 101. Thus the charged airborne particles generated by the wire electrode 303 are attracted into the inactivation zone that is about the plasma generator and specifically, in the case of the cylindrical coil 101, the inactivation zone extends outwardly circumferentially about the cylindrical coil 101. The inactivation zone extends outwardly from the outer surface of the cylindrical coil 101 by a distance of about 1-2 cm. Once the airborne particles enter into the inactivation zone, then they are rendered harmless as the plasma discharge destroys all pathogens and inactivates all undesirable airborne particles. It is to be understood that some of the airborne particles will then precipitate onto the coil 101. However, it is not essential that all airborne particles precipitate onto the plasma generator cylindrical coil 101 for the plasma coil electrostatic precipitator assembly 100 to operate effectively to remove undesirable airborne particles from the air flow that is flowing by the assembly 100. Indeed, it is to be understood that it is not desirable that all airborne particles precipitate onto the plasma generator cylindrical coil 101. All that is required is that the airborne particles are attracted into the inactivation zone for the plasma coil electrostatic precipitator assembly 100 to operate effectively.

The insulating support 302 ensures that power is not provided to a surface on which the electrostatic wire electrode assembly 301 is mounted.

The wire of the wire electrode 303 is of a suitably thin wiring gauge so that the surface area of the wire electrode 303 is minimal. For example, an America wire gauge (AWG) value of 38 (0.1 mm diameter) or higher (<0.1 mm diameter) has been found to be suitable. It will be appreciated by those skilled in the art that a wire of any gauge may be used provided it does not significantly impede air flow there through. For a larger scale electrostatic wire electrode assembly 301, a larger gauge wire would be necessary.

FIG. 4 shows the electrostatic wire electrode assembly 301 from the opposite side as shown in FIG. 3. The looped arrangement of the wire to form the wire electrode 303 on the support 302 can be better appreciated from this view. The wire is looped between opposite sides of the insulating support 302. A grid arrangement for the wire electrode 303 is shown with vertical wire sections that are parallel to each other. However, a grid arrangement wherein further wire sections intersect each other may also be used. Alternatively, a grid arrangement wherein the wire segments of FIG. 4 are arranged horizontally may be employed. As will be appreciated by those skilled in the art, any arrangement that places sufficient charge on air particles passing through the wire electrode 303 without unduly impeding air flow may be used in the electrostatic wire electrode assembly 301 of the present teachings. The direction of the air flow is indicated by the arrow "A".

Further details and features of the coil assembly 201 are now described with reference to FIGS. 5, 6 and 7. As shown in FIG. 5, the plasma coil assembly 201 requires a high voltage power supply 501 to operate. The plasma coil assembly 201 is configured to operate at a power density less than 1 W/cm2 to operably generate a plasma discharge.

In the preferred embodiment, the plasma generator comprises a generally cylindrical coil assembly, which is configured to operate at a power density less than 1 W/cm2 to operably generate a plasma discharge circumferentially about a longitudinal axis of the coil assembly. Most preferably, the plasma generator is configured to be operated at a power density in the range from 0.1 to 0.5 W/cm2. This is a relatively low power density for plasma generation and is effective for creating an inactivation zone about the plasma generator. Electrical contacts 502, which in the embodiment shown in FIGS. 5 to 7, are provided on the insulated stands 204, are used for applying high voltage to the plasma generating cylindrical coil 101. As can be appreciated from FIG. 5, the insulated stands 204 act as a set of support holders and the cylindrical coil 101 is detachable from the insulating stands 204. The cylindrical coil 101 is removably engageable with the insulated stands 204 which function as support holders for the cylindrical coil 101. In particular, the insulator caps 203 of the cylindrical coil 101 are adapted to engage with the insulating stands 204 as the dimensions of the insulator caps 203 and the dimensions of the insulating stands 204 are configured to correspond such that the insulator caps 203 can be engaged with the insulating stands 204 in a tight fit engagement by pushing each insulator cap 203 into its respective insulating stand 204. Particularly, the width of the insulator caps 203 are the same as the width of the insulating stands 204 so as to provide a tight fit between the insulating stands 204 and the insulator caps 203. Furthermore, the insulating stands 204 are provided with an arcuate ledge 205 against which the insulator caps 203 abut when the insulator caps 203 are inserted in the insulating stands 204. The arcuate support ledge 205 acts as a stop against the insulator caps 203 being pushed any further down into the insulating stands 204 and the arcuate support ledge 205 also supports the cylindrical coil 201 in position so that it is optimally located to allow air flow above and below the cylindrical coil 101. It will be appreciated that the cylindrical coil 101 can be easily removed and replaced in the embodiment presented herein. This involves simply retracting the dielectric retainers 202 from contact with the insulator caps 203 and lifting the cylindrical coil 101 in the direction of the arrows shown.

It should be appreciated that one of the main advantages of the plasma coil assembly 201 of the present teaching is that cylindrical coil 101 can be easily replaced like changing a battery or a light bulb.

It will also be understood by those skilled in the art that power is provided from the power supply 501 to the electrical contacts 502. The exact nature of the connection (e.g., wiring) between the contacts 502 and the power supply can be chosen as appropriate and it is not necessary that the power supply 501 and the coil assembly 201 be collocated. The power from the power supply 501 is then passed through contacts 502 on the insulated stands 204 to the electrical contacts 503 of the cylindrical coil 101. As indicated above, the plasma coil assembly 201 is configured to operate at a power density less than 1 W/cm2 to operably generate a plasma discharge. Most preferably, the plasma generator is configured to be operated at a power density in the range from 0.1 to 0.5 W/cm2.

A transformer (not shown) may also be used between the power supply and the contacts 503 to provide high-voltage alternating current. The power supply 501 may also be used to provide power to the electrostatic wire electrode assembly 301 of the present teachings. Again the specific wiring configuration can be chosen as appropriate by those skilled in the art.

Figure 6:
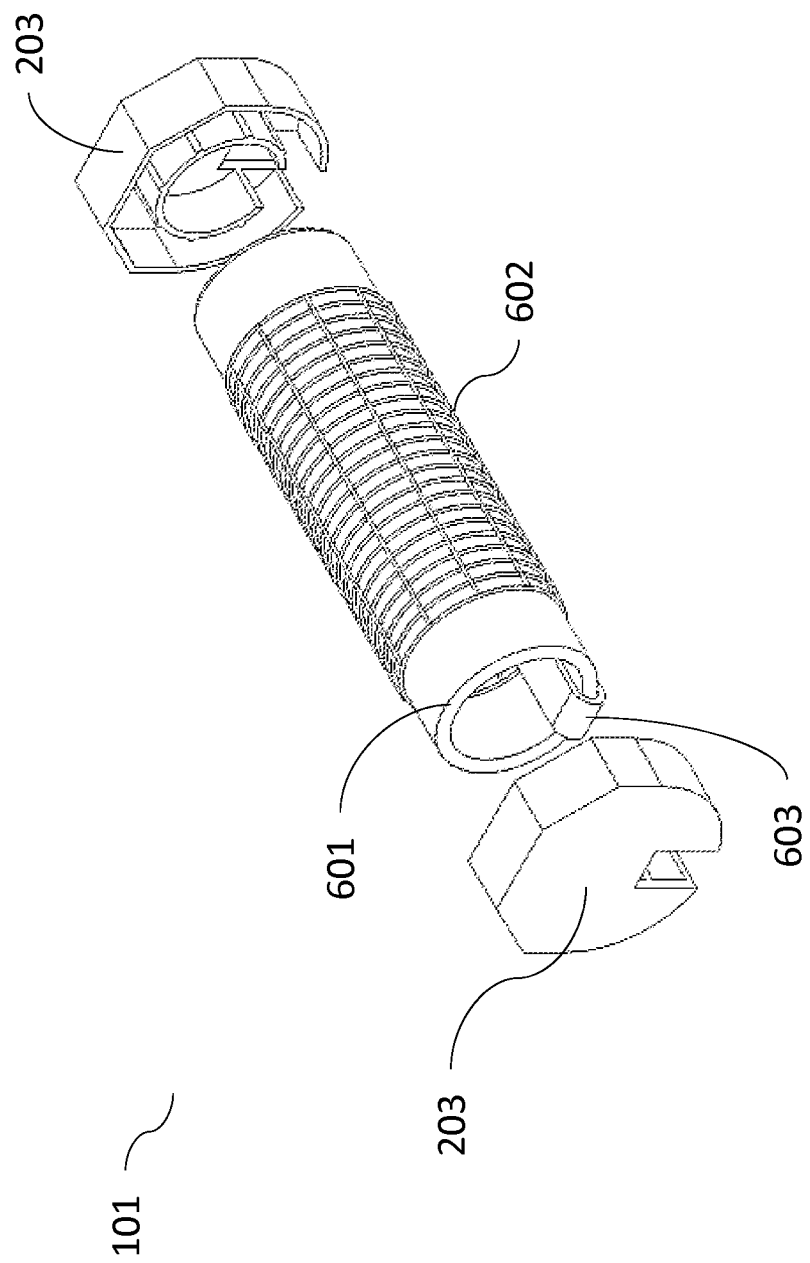
FIG. 6 is a view of the cylindrical coil of FIG. 5.

FIG. 6 is a perspective view of the cylindrical coil 101 when removed from the insulating stands 204. It can be seen that the cylindrical coil includes a dielectric insulator tube 601 and an outer mesh electrode 602. A first electrical contact 603 is also provided, which will be explained in more detail.

Figure 7:
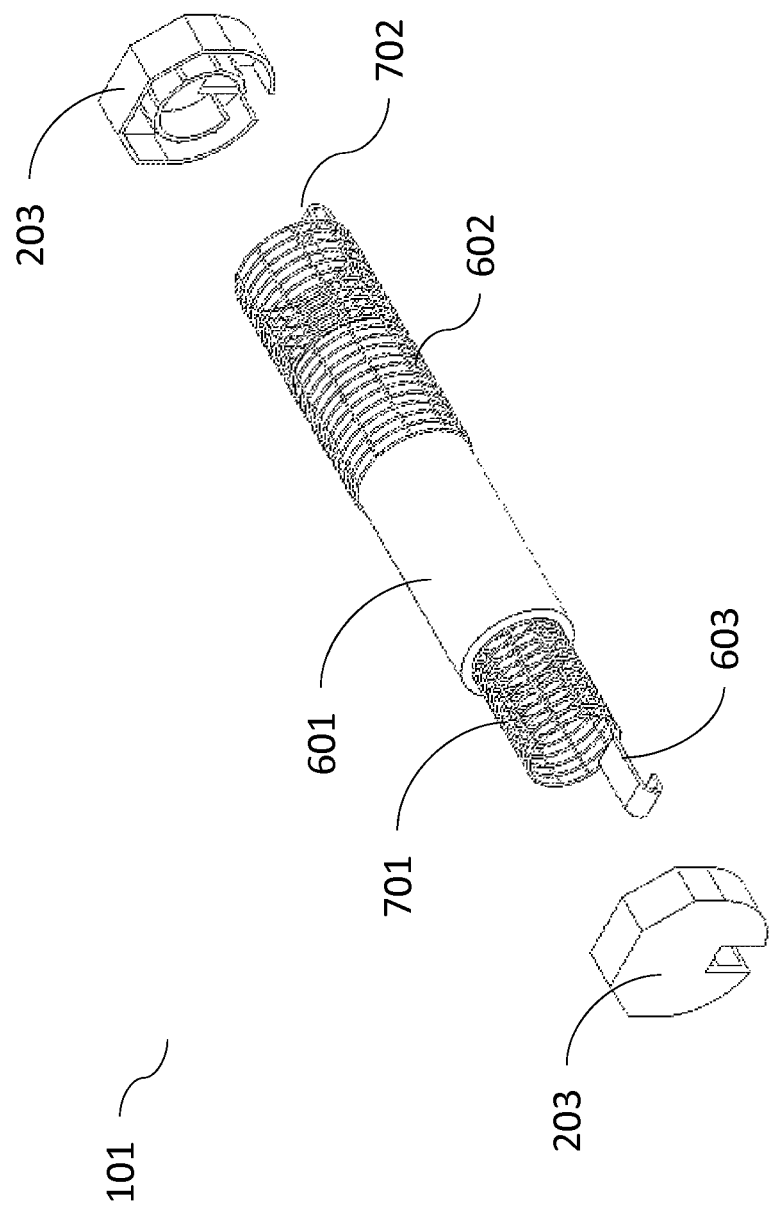
FIG. 7 is an expanded view of the cylindrical coil of FIG. 6.

FIG. 7 is a perspective view of the cylindrical coil of FIG. 6 with the outer mesh electrode 602 offset such that it is only partially overlapping the dielectric insulator tube 601. In addition, an inner mesh coil acting as an inner electrode 701 is also shown extending from within the insulator tube 601 for ease of viewing. Operably, the inner mesh coil 701 is fully enclosed within the dielectric insulator tube 601. It can also be appreciated that the first electrical contact 603 is directly attached to the inner electrode 701 such that power is supplied directly to the mesh coil of this electrode 701. Another electrical contact 702 is attached to the outer electrode 602.

The inner and outer wire meshes, which act as inner 701 and outer electrodes 602, maintain direct contact around their respective total surface areas with the dielectric tube 601. This ensures that there are no air pockets around the cylindrical coil where elevated levels of plasma can build up during generation of plasma.

Plasma discharge is generated at the coil 101 by applying power to the pair of electrodes, that is, the inner electrode 701 and the outer electrode 602. The applied power sustains either a DC or an AC discharge between, around and/or on the surface of said electrode pair.

The plasma generation in the present teachings is of a dielectric barrier discharge (DBD) type with an inner wire mesh cylinder 701 insulated by a dielectric glass tube 601. The cylindrical shape of the coil 101 ensures that the outer mesh 602 extends completely circumferentially around the cylindrical coil and that plasma is discharged evenly in all directions from the cylindrical coil.

Dielectric-barrier discharge (DBD) is an electrical discharge between two electrodes separated by an insulating dielectric barrier. Known DBD devices are typically planar, using parallel plates separated by a dielectric or cylindrical, using coaxial plates with a dielectric tube between them. In one coaxial configuration, the dielectric is shaped in the same form as common fluorescent tubing. It is filled at atmospheric pressure with either a rare gas or rare gas-halide mix, with the glass walls acting as the dielectric barrier. Due to the atmospheric pressure level, such processes require high energy levels to sustain. Common dielectric materials include glass, quartz, ceramics and polymers.

Figure 8:
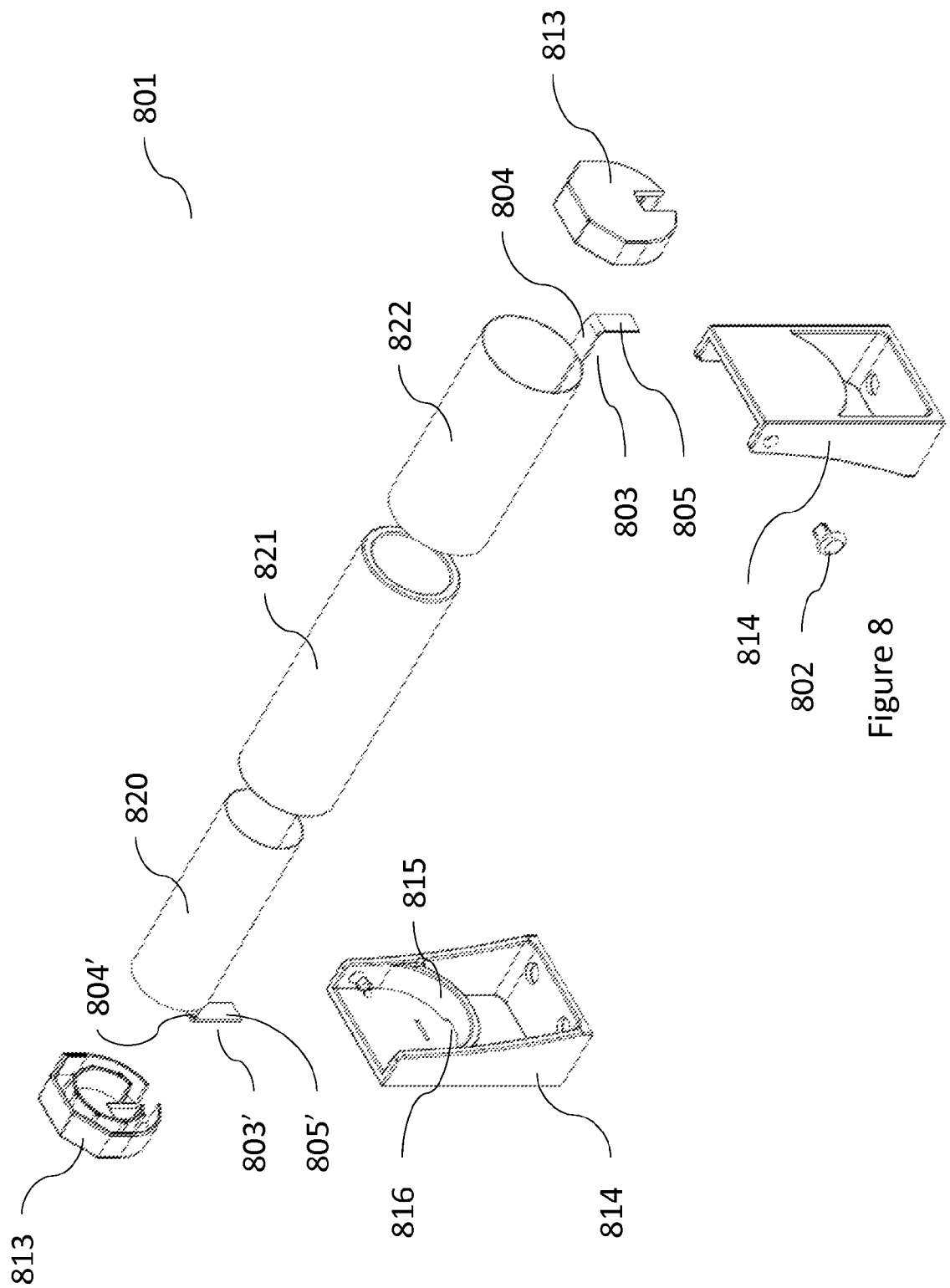
FIG. 8 is an expanded view of an alternative embodiment of the coil assembly shown in expanded view in FIGS. 5 to 7.
Figure 9:
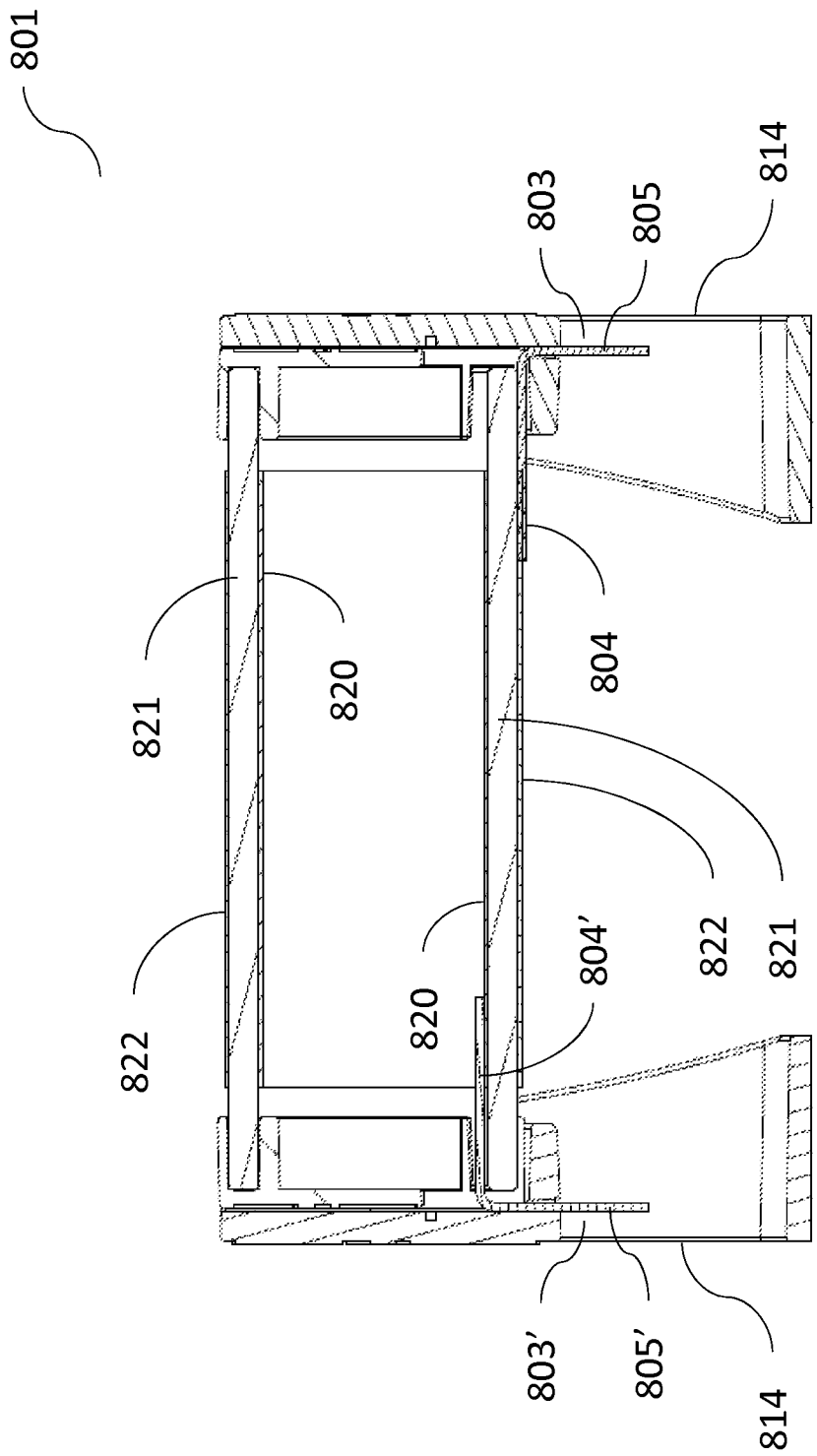
FIG. 9 is a cross sectional view of the coil assembly shown in FIG. 8 with the coil assembly inserted in the insulating stands provided at each end of the coil assembly and showing the electrical contacts located through the slots provided in the insulating stands; and configured for connection to a power source.

FIGS. 8 and 9 show an alternative embodiment of the plasma generator cylindrical coil indicated generally by reference numeral 801. Like numerals indicate like features between FIGS. 5 to 7 and FIGS. 8 to 9. Similarly to described above with reference to FIGS. 5 to 7, the cylindrical coil 801 is removably engageable with the insulated stands 814 which function as support holders for the cylindrical coil 801. In particular, the insulator caps 813 of the cylindrical coil 801 are adapted to engage with the insulating stands 814 as the dimensions of the insulator caps 813 and the dimensions of the insulating stands 814 are configured to correspond such that the insulator caps 813 can be engaged with the insulating stands 4 in a tight fit engagement by pushing each insulator cap 813 into its respective insulating stand 814. Particularly, the width of the insulator caps 813 are the same as the width of the insulating stands 814 so as to provide a tight fit between the insulating stands 814 and the insulator caps 813. Furthermore, the insulating stands 814 are provided with an arcuate ledge 815 against which the insulator caps 203 abut when the insulator caps 813 are inserted in the insulating stands 814. It will be noted that in this embodiment, each arcuate support ledge 815 comprises a slot 816. The arcuate support ledge 215 acts as a stop against the insulator caps 813 being pushed any further down into the insulating stands 814 and the arcuate support ledge 215 also supports the cylindrical coil 801 in position so that it is optimally located to allow air flow above and below the cylindrical coil 801. It will be appreciated that the cylindrical coil 801 can be easily removed and replaced in the embodiment presented herein. This involves simply retracting the dielectric retainers 802 from contact with the insulator caps 813 and lifting the cylindrical coil 801 in the direction of the arrows shown.

Figure 5:
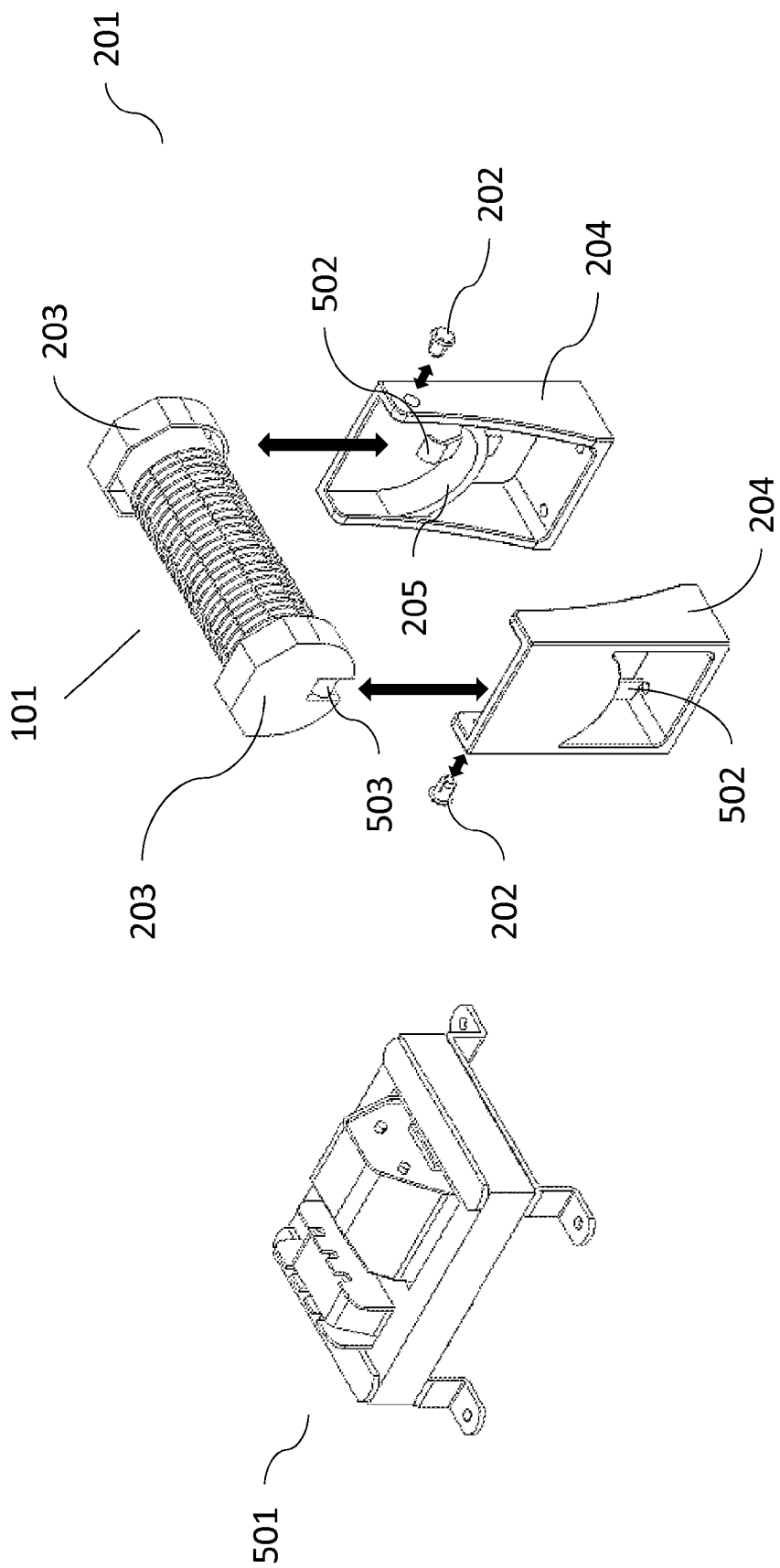
FIG. 5 is an expanded view of the coil assembly of FIG. 1 as well as a high voltage power supply.

An alternative embodiment of the cylindrical coil 801 shown in FIGS. 8 and 9 comprises an alternative arrangement of the electrical contacts 803, 803' for the cylindrical coil 801, in particular, the arrangement of the electrical contacts for power supply to the inner mesh 820 and outer mesh 822 of the plasma generating cylindrical coil 801. [Note that, purely for simplicity, the inner mesh 820 and the outer mesh 822 are shown in FIGS. 8 and 9 as cylinders; however, it is to be understood that the inner mesh 820 and outer mesh 822 of FIGS. 8 and 9 comprise the same mesh structures as indicated by reference numerals 701, 602 respectively, shown in FIGS. 5 to 7]. The operation of the plasma coil electrostatic precipitator assembly 100 is the same when comprising either the cylindrical coil 101 shown in FIGS. 5 to 7; or the cylindrical coil 801 shown in FIGS. 8 and 9. FIG. 8 is a perspective view of the cylindrical coil 801 when removed from the insulating stands 814. The cylindrical coil 801 includes a dielectric insulator tube and an outer mesh electrode as in cylindrical coil 101. In this embodiment, electrical contacts 803, 803' are also provided, as will be explained in more detail below.

Referring now to FIG. 9, there is shown a cross sectional view of the cylindrical coil 801 of FIG. 8 with the outer mesh electrode 822 offset such that it is only partially overlapping the dielectric insulator tube 821. The coil assembly 801 comprises an inner mesh coil 820 to function as an inner electrode 820. Operably, the inner mesh coil 820 is fully enclosed within the dielectric insulator tube 821. It can also be seen from FIG. 9 that the first electrical contact 803 is directly attached to the outer electrode 822 such that power is supplied directly to the mesh coil of this electrode 822. Another electrical contact 803' is attached to the inner electrode 820. Each electrical contact 803, 803' comprises a first limb 804, 804' and a second limb 805, 805'. In this way, each electrical contact 803, 803' is generally in the form of an L-shaped member comprised of the two limbs 804, 804'; 805,805', respectively. As can be seen in FIG. 9, the first limb 804' is directly in contact with the inner electrode 820 and the second limb 805' is, in use, inserted through the slot 816 provided on the arcuate support ledge 815 of the insulating stand 814 so that the second limb 805' extends downwardly from below the arcuate support ledge 815 and is available within the lower section of the insulating stand 814, for connection to a power source. Also as shown in FIG. 9, the electrical contact 803 is attached to the outer electrode 822 with the first limb 804 of electrical contact 803 being directly in contact with the outer electrode 822 and the second limb 805 is, in use, inserted through the slot 816 of the insulating stand 814 and the second limb 805 is available within the open section of the insulating stand 814, for connection to a power source.

The inner wire mesh 820 and outer wire mesh 822, which act as inner electrode 820 and outer electrode 822, maintain direct contact around their respective total surface areas with the dielectric tube 821. This ensures that there are no air pockets around the cylindrical coil where elevated levels of plasma can build up during generation of plasma.

It will be understood that the plasma generation in the present teachings is of a dielectric barrier discharge (DBD) type with the inner wire mesh cylindrical electrode 701, 820 insulated by a dielectric glass tube 601, 821. The cylindrical shape of the coil 101, 801 ensures that the outer mesh 602,822 extends completely circumferentially around the cylindrical coil plasma generator 101,801 and that plasma is discharged evenly in all directions from the cylindrical coil 101, 801.

Figure 16:
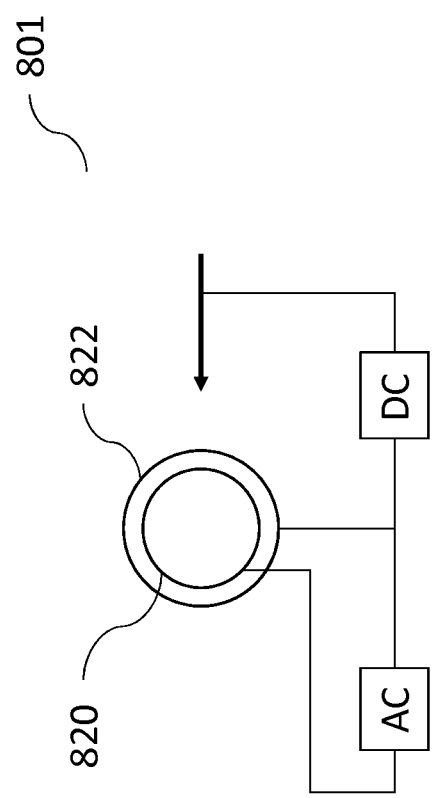
FIG. 16 is a schematic diagram showing the connection for power supply to the inner mesh and the outer mesh of the coil assembly.

Plasma discharge is generated at the coil 801 by applying power to the pair of electrodes, that is, the inner electrode 820 and the outer electrode 822. The applied power sustains either a DC or an AC discharge between, around and/or on the surface of the electrode pair comprised of the inner electrode 820 and the outer electrode 822. It is to be understood that the arrangement shown in FIG. 16 shows only one embodiment of the arrangement for the cylindrical coil 801 and also for the cylindrical coil 101 which is shown as being an AC voltage supply to the inner electrode 820 and the outer electrode 822. As also shown in FIG. 16, in this particular embodiment, a DC voltage such as in the range of between 1,000 V and 10,000 V (1 kV to 10 kV); preferably in the range of between 2,000 and 9,000 volts; more preferably in the range of between 3,000 and 8,000 volts; most preferably in the range of between 4,000 and 7,000 volts; and ideally, is at a voltage of about 5,000 volts, is applied between the electrostatic precipitator such as the wire electrode, cylindrical electrode or the needle electrode array; and the outer mesh of the cylindrical coil plasma generator 101,801.

It will be appreciated that the voltage and current parameters required to achieve a dielectric barrier discharge will depend principally on the nature of the dielectric used. In general, operating voltages below 1 kV are not practical, and preferably, an operating voltage in the range from 1 to 6 kV is provided between the inner and outer mesh electrodes, most desirably, a voltage of from 3 to 5 kV is provided between the inner and outer mesh electrodes, for example about 4 kV. It will be appreciated that the current required to maintain the dielectric barrier discharge is significantly less than that required to initiate it. The current (and hence the power) of plasma generator units is normally expressed in terms of the starting current. There should be used a (starting) current in the range from 1 to 10 mA, preferably at least 3 mA. The power of the plasma generator will, of course, depend on the voltage and current combination. The power should generally be not more than 50 watts, and is preferably at least 4 watts. Typically, the power is in the range from 10 to 40 watts. These power levels have in particular been found to be convenient where the plasma generator is used as part of an apparatus unit having a conduit volume of the order of 0.02 to 1.0 m3.

Having explained each of the individual components of the plasma coil electrostatic precipitator assembly 100, the operation of the assembly 100 i.e., the interaction of these components and the cooperation between the plasma coil assembly 201 and the electrostatic precipitator 301, will now be described.

Figure 10:
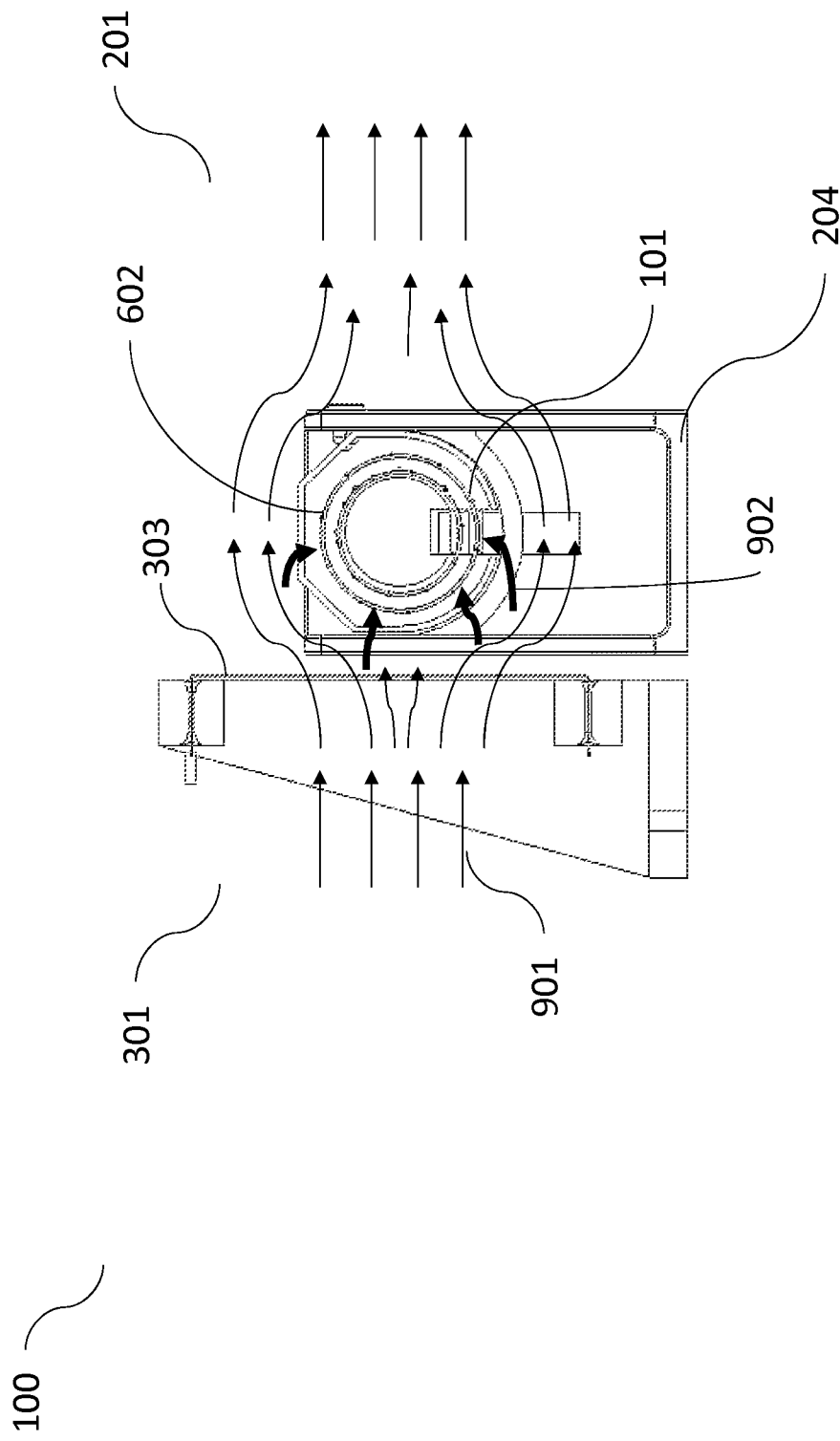
FIG. 10 is a side view of the plasma coil electrostatic precipitator assembly of FIG. 1 as air flows past it.

Turning to FIG. 10, a side view of the plasma coil electrostatic precipitator assembly 100 is shown. It can be seen that the coil assembly 201 is positioned adjacent the electrostatic wire electrode assembly 301.

High DC voltage bias is applied between the electrostatic wire electrode 303 of the electrode assembly 301 and the outer wire mesh electrode 602 of the coil assembly 201. The aforementioned high voltage power supply 501 in conjunction with a transformer(s) may be used to apply the voltage. The polarity of the voltage applied is such that the wire electrode 303 is negatively biased with respect to the outer wire mesh electrode 602 of the coil 101.

It should be appreciated that the surface area of the wire electrode 303 is significantly smaller than that of the outer wire mesh electrode 602 in order to allow for the correct operation of an electrostatic device between said electrodes 303 and 602. As is known to those skilled in the art, the negatively biased wire electrode 303 should be pointed i.e., it should have a small area to enhance the electric field around it and promote the emission of electrons. On the other side, for the coil 101, the function is to collect the charged particles (not electron emission), therefore the surface area does not have to be small as that of the wire electrode 303, where an enhanced electric field is not needed.

Furthermore, the distance between the wire electrode 303 and the outer wire mesh electrode 613 is chosen to allow for the correct operation of an electrostatic device between said electrodes. The distance should be optimized for a given high voltage bias applied between said electrodes. If these are too close, there will be arcing between them that releases too many electrons, causing damage to the electrodes and generating too many anti-pathogenic agents. On the other hand if they are too distant from each other, the electric field on the wire electrode may not be high enough resulting in low electron emission and poor particle charging performance.

Airborne particles in the airflow 901, carrying pollutants and pathogens, are electrostatically charged by the wire electrode 303. Specifically, airborne particles collect electrons emitted by the wire electrode 303 which is negatively biased with respect to the outer wire mesh electrode 602. The charged airborne particles are then attracted to and collected by the outer wire mesh electrode 602, effectively removing them from the air flow 901. The flow of airborne particles and contaminants in the air flow 901 towards the outer wire mesh assembly 602 is shown by arrows 902 in FIG. 10.

The generation of plasma by the coil 101 creates an inactivation zone around the coil 101. An inactivation zone is a zone in which plasma is released and is effective to inactivate airborne pollutant material including pathogens, collected on the electrode 602 and entrained in the air flow 901. Such airborne pollutant material (airborne pollutants), which can be health threatening, may be subdivided into three groups: (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air. The plasma generated by the coil 101 is effective to inactivate any of the airborne pollutant materials as defined in subdivisions (a) to (c).

It can also be seen from FIG. 10 that the insulating stands 204 acting as support holders raise or elevate the cylindrical coil 101 above any surface to which the coil assembly 201 may be attached. Such a raised configuration of the coil 101 allows air circulation above and below the coil 101 as shown by the air flow 901. Specifically, by having the electrode assembly raised, an inactivation zone extends circumferentially around the cylindrical coil; and air can pass both above and below the cylindrical coil 101 while being subjected to the same level of plasma. The air flows in a direction that is perpendicular to the orientation of the coil 101 ensuring air exposure to said coil is maximized.

FIG. 11 details the main steps in the operation of the plasma coil electrostatic precipitator assembly 100 of the present invention. An impeller, such as a fan, forces air flow through an air treatment device or ducting housing the plasma coil electrostatic precipitator assembly 100 (step 901). The air flow generated forces air and airborne particles and contaminants through the electrostatic electrode wire assembly 301 (step 902). The airborne particles and contaminants are brought to the vicinity of the wire electrode 303 which emits electrons and charges said particles and contaminants with a negative charge (step 903). The air flow forces the charged particles and contaminants towards the vicinity of the coil 101 (step 904). The outer electrode 602 of the coil 101 has a positive charge and therefore the negatively charged airborne particles and contaminants are attracted and collected by the outer wire mesh electrode 602 (step 905). Finally, pathogens present in the collected airborne particles and contaminants are exposed to the plasma discharge for extended periods of time resulting in continuous degradation ensuring total inactivation (step 906). In addition, any particles or pathogens which remain airborne i.e., not collected by the coil 101 but which are in the aforementioned inactivation zone are inactivated by the plasma discharge from the coil 101.

It should be appreciated that while the plasma concentration in the aforementioned inactivating zone, created by the coil assembly 201, is sufficient to effectively inactivate airborne pollutant material entrained in the air flow as well as in the collected particles it is desirable to maintain the concentration of plasma sufficiently low so that the concentration any anti-pathogenic agents created by the plasma discharge in the inactivating zone is at a physiologically acceptable level in the cleaned air expelled by the air treatment apparatus. The electrostatic precipitation feature of the present teaching is designed to attract airborne particles and contaminants into the inactivation zone created by the plasma discharge zone about the plasma generator; and allows for a reduction in the output of anti-pathogenic by-products from an air treatment device having the plasma coil electrostatic precipitator assembly 100 therein. This reduction is achieved by safely reducing the supply of power that sustains the plasma discharge at the coil 101 while retaining a high inactivation efficacy. It is to be understood that attracting the airborne particles and contaminants into the inactivation zone created by the plasma discharge zone about the plasma generator inactivates all the airborne particles and contaminants while resulting in some, but not, necessarily or desirably, all of those airborne particles and contaminants precipitating and collecting on the coil 101.

The plasma coil electrostatic precipitator assembly 100 of the present invention may also be employed within a ducting system or conduit. In such a configuration, air is directed or forced around the plasma discharge from the coil 101 through a ducting system. The ducting system is designed to ensure that all air flow about the plasma discharge is within 1 centimeter of the discharge. It is appreciated said ducting improves the particle and contaminant collection by the outer wire mesh electrode 602. Furthermore, said ducting may comprise electrostatically charged electrodes on its internal surface, negatively charged, to repel negatively charge airborne particles and contaminants to improve collection by the outer wire mesh electrode 602. Specifically, particles that are negatively charged by the electrode assembly 301 are repelled by the (negatively charged) internal surfaces of the ducting and attracted to the positively charged mesh electrode 602.

Figure 12:
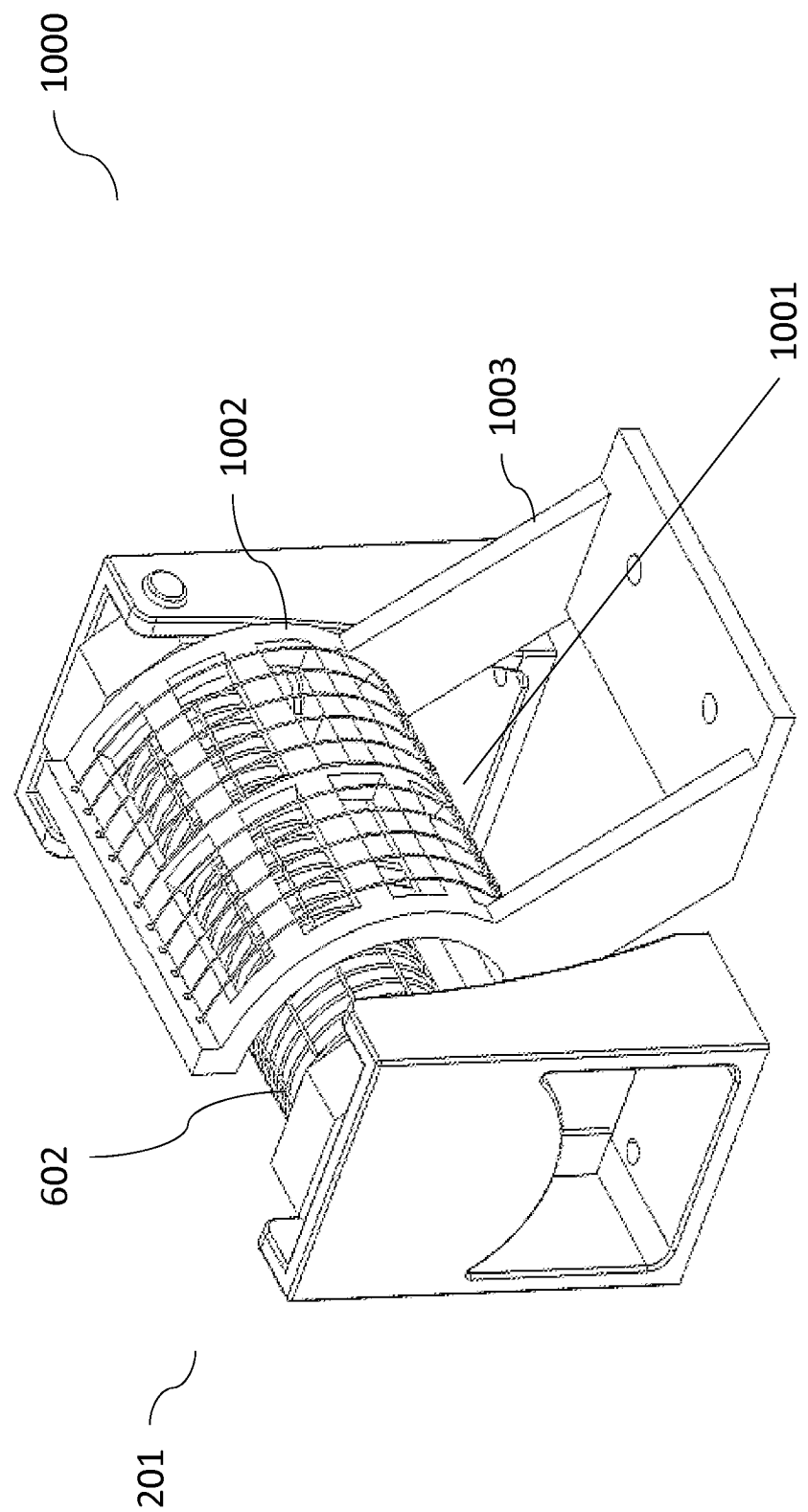
FIG. 12 is a perspective view of another embodiment of the plasma coil electrostatic precipitator assembly in accordance with the present teachings.

FIG. 12 shows another embodiment of the plasma coil electrostatic precipitator assembly of the present invention. In the configuration of FIG. 12, the plasma coil electrostatic precipitator assembly 1000 uses the same coil assembly 201 as the previous embodiment. However the electrode assembly 1001 is different. In particular, the vertical wire electrode 303 of the previous embodiment is replaced by a concentric wire electrode 1002 held in place by an insulating support 1003.

As in the previous embodiment, the concentric wire electrode 1002 is negatively charged with respect to the outer wire mesh electrode 602 and air flow is forced through the concentric wire electrode 1002. Particles in the air are negatively charged by the wire electrode 1002 and attracted to the positively charged mesh electrode 602. The particles subsequently collect on the mesh electrode 602 and are exposed to plasma generated by the coil assembly 201.

It will be appreciated that the advantage of the configuration of the electrode assembly 1001 is that by having the wire electrode 1002 concentric to the outer wire mesh electrode 601, the distance between both electrodes is constant resulting in optimized performance of the plasma coil electrostatic precipitator assembly.

Figure 13:
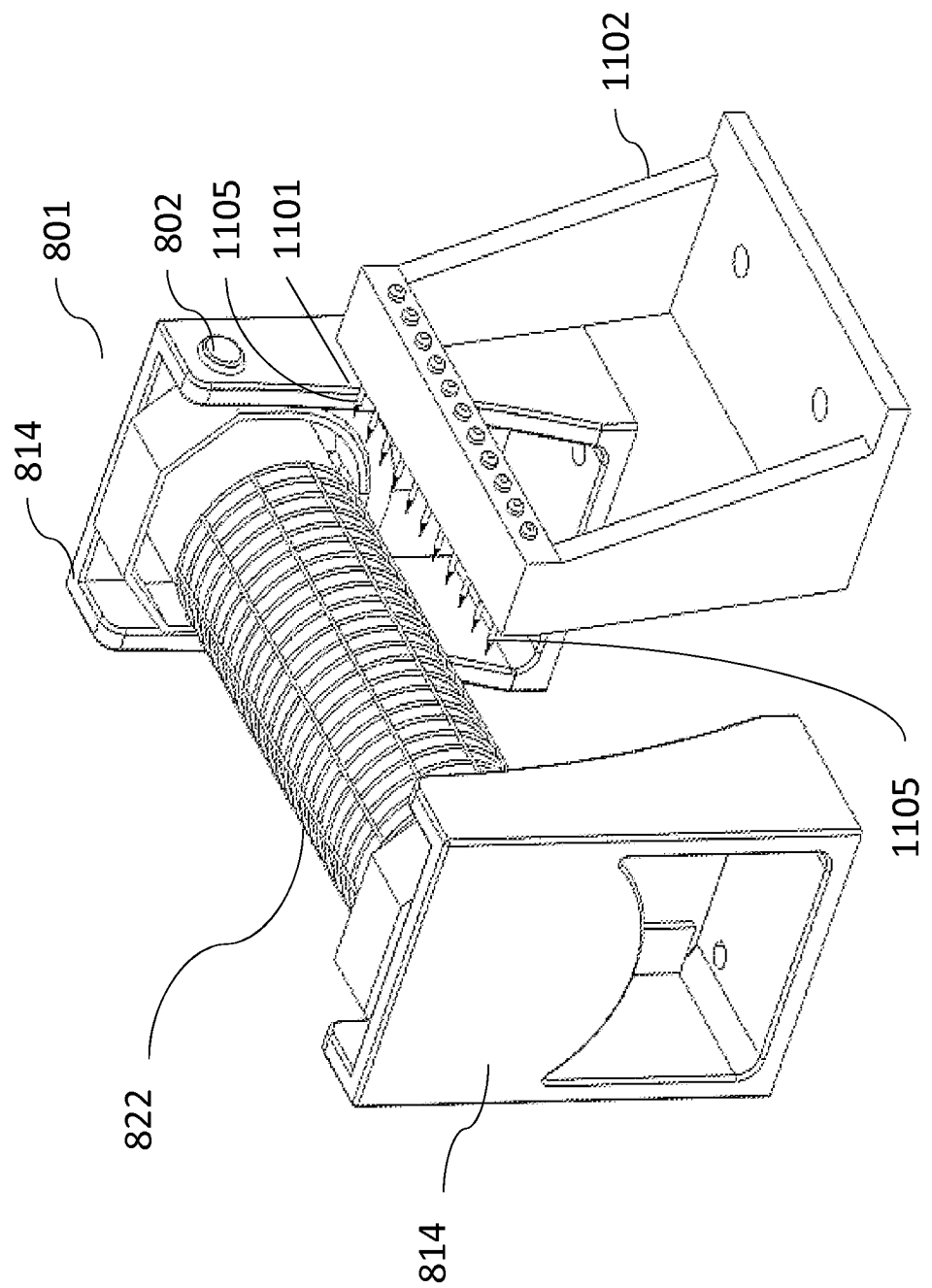
FIG. 13 is a perspective view of a further embodiment of the plasma coil electrostatic precipitator assembly in accordance with the present teachings.

FIG. 13 shows a preferred embodiment of the plasma coil electrostatic precipitator assembly of the present invention. In this embodiment, the vertical wire electrode 303 is replaced by a linear needle electrode 1101 which is held in place by an insulating support 1102. It can be seen from FIG. 13 that the insulating stands 814 function to raise or elevate the cylindrical coil 801 above any surface to which the coil assembly 801 may be attached. Such a raised configuration of the coil 801 allows air to flow above and below the coil 801 in the same way as shown in FIG. 10. Specifically, by having the electrode assembly comprising the inner electrode 820 and the outer electrode 822 raised, an inactivation zone extends completely around the cylindrical coil 801 and air can pass both above and below the cylindrical coil 801 while being subjected to the same level of plasma. The air flows in a direction that is perpendicular to the orientation of the coil 801, thus ensuring that charged airborne pollutant material in that air flow after the air has passed the linear needle electrode array 1101, is attracted into the inactivation zone. The inactivation zone extends outwardly from the plasma generator by approximately 1 cm to 2 cm; in the embodiment shown in which the plasma generator comprises a cylindrical coil assembly, the inactivation zone extends outwardly from the cylindrical coil by approximately 1 cm to 2 cm, circumferentially about the cylindrical coil.

The linear needle electrode array 1101 comprises a plurality of needle electrodes 1105 having a sharp tip 1106. The linear needle electrode array 1101 may be considered as a single linear array of needle electrodes and although only one line of electrodes is shown in FIG. 11, in an alternative embodiment, a plurality of rows of needle electrodes 1105 may be provided, for instance in parallel to each other, on the needle electrode. For instance, a plurality of parallel linear needle electrode arrays may be provided on the electrode. Other arrangements of needle electrode arrays may also be provided.

Figure 14:
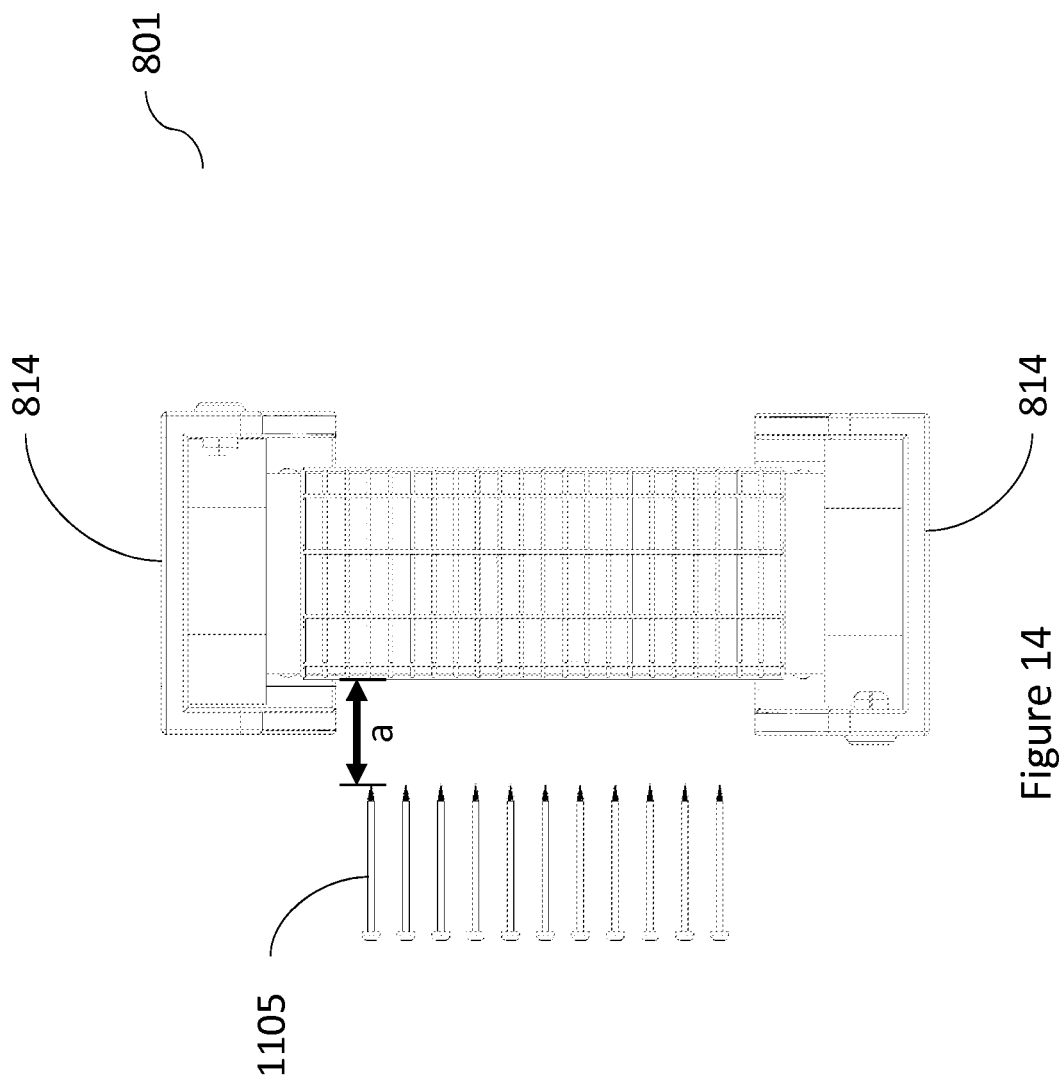
FIG. 14 is a plan view of the coil assembly of FIG. 13 showing the arrangement of the array of needles of the electrode.
Figure 15:
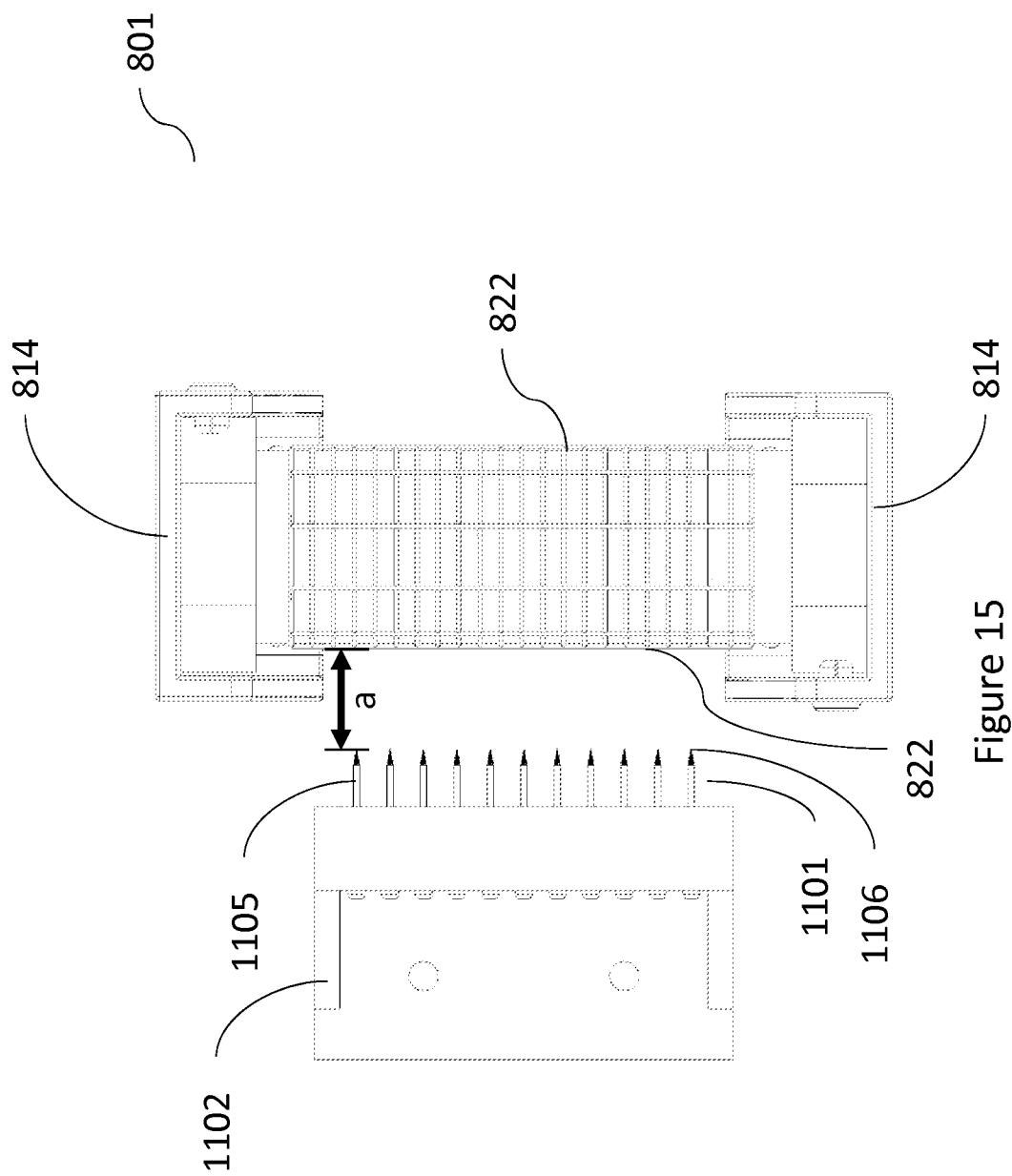
FIG. 15 is a perspective view of the coil assembly of FIGS. 13 and 14.

As shown in FIGS. 14 and 15, the electrode 1101 is located at a pre-determined distance from the electrostatic precipitator 801 (or the electrostatic precipitator 101). The pre-determined distance is measured as the distance from the electrode, be it a wire electrode or tip of a needle electrode or other form of electrode; to the closest point on the outer surface of the outer mesh electrode 602. For instance, as shown in FIG. 14, the distance from each needle tip 1106 of each needle electrode 1105 to the outer surface of the outer mesh electrode 822 is indicated by the letter a. This predetermined distance "a" is configured to prevent arcing between the needle electrode 1101 and the electrostatic precipitator 801 (or 101) while at the same time, allowing cooperation between the needle electrode electrostatic precipitator and the plasma generator such that the charged airborne particles, charged by the needle electrode electrostatic precipitator are attracted into the inactivation zone about the plasma generator. This predetermined distance is in the range of from 0.5 cm to 2 cm; and preferably the distance is approximately 1 cm.

As in the previously described embodiments, high DC voltage bias is applied between the needles 1105 of the needle electrode array 1101 and the outer wire mesh electrode 822 of the coil assembly 801. The aforementioned high voltage power supply 501 in conjunction with a transformer(s) may be used to apply the voltage. The polarity of the voltage applied is such that the needle electrode array 1101 is negatively biased with respect to the outer wire mesh electrode 822 of the plasma generating coil assembly 801. The voltage is set to ensure that the negatively charged airborne particles in the air flow from the needle electrode array 1101 are attracted towards the outer wire mesh electrode 822 of the coil assembly 801. The voltage is set at a level so as to attract the charged airborne particles including charged airborne pollutant materials comprising pathogens into the inactivation zone so that the airborne pollutant materials are rendered inactive and harmless. The inactivation zone extends outwardly from the cylindrical coil by approximately 1 cm to 2 cm circumferentially around the cylindrical coil. The voltage between the needle electrode array 1101 and the outer wire mesh electrode 822 of the coil assembly 801 is in the range of between of between 1,000 and 10,000 volts; preferably in the range of between 2,000 and 9,000; more preferably in the range of between 3,000 and 8,000 volts; most preferably in the range of between 4,000 and 7,000 volts; and ideally, at about 5,000 volts.

Thus the needle electrode array 1101 is negatively charged with respect to the outer wire mesh electrode 602. Air flow is forced past the needle electrode 1101 and towards the electrostatic precipitator 801. It will be appreciated that the advantage of the needle electrode array 1101 is that the sharp tips 1106 of the needle electrodes 1105 result in higher electron emission by the needle electrodes 1105 of the needle electrode array 1101 resulting in optimized electrostatic precipitation performance. Said advantage may be also used to reduce the DC high voltage difference between the electrostatic precipitator electrode 1101 and the coil 101 which contributes to lower emission of anti-pathogenic by products by the plasma discharge while maintaining inactivation efficacy.

It will be appreciated that the present teachings provide an air treatment device to attract airborne pathogens to the vicinity of the plasma discharge and to keep them exposed to the plasma discharge and the anti-pathogenic by-products generated by the device for as long as possible. Furthermore, device captures said airborne pathogens on the surface of an electrode assembly on to which said plasma discharge is generated to optimize inactivation efficacy.

It will also be understood that the above description of a plasma coil electrostatic precipitator assembly with reference to separate embodiments is not intended to convey the limitation that features or components that are described with reference to one embodiment cannot be used or interchanged for those described with reference to a second embodiment. The words comprises/comprising when used in this specification are to specify the presence of stated features, integers, steps or components but does not preclude the presence or addition of one or more other features, integers, steps, components or groups thereof.

We claim:

1. An air treatment device comprising:

an electrostatic precipitator configured to charge airborne particles in the vicinity of the electrostatic precipitator; and a plasma generator positioned in proximity to the electrostatic precipitator and configured for cooperation with the electrostatic precipitator, the plasma generator configured to discharge plasma and provide an inactivation zone in the region of the plasma generator operable to inactivate airborne particles; and wherein the air treatment device comprises means for directing the charged airborne particles generated by the electrostatic precipitator into the inactivation zone such that the air treatment device is adapted to generate charged airborne particles and to direct the charged airborne particles into the inactivation zone so as to expose the charged airborne particles to plasma in the inactivation zone; and, wherein the plasma generator includes a coil assembly comprising a cylindrical coil and an insulating stand at each of a first and second end of the cylindrical coil configured for mounting the cylindrical coil in an elevated position.

2. The air treatment device of claim 1 wherein the electrostatic precipitator comprises an electrode held by an insulating support.

3. The air treatment device of claim 2 wherein the electrode comprises a wire electrode including a single wire looped and oriented in the vertical direction.

4. The air treatment device of claim 2 wherein the insulating support comprises an opening configured to allow air to flow therethrough and the wire of the wire electrode forms a grid over the opening.

5. The air treatment device of claim 3 wherein the wire electrode is an arcuate electrode, and wherein the arcuate electrode and the cylindrical coil are concentric to each other.

6. The air treatment device of claim 2 wherein the electrode comprises a linear array of needle electrodes.

7. The air treatment device of claim 1 wherein the cylindrical coil includes a cylindrical inner mesh, a cylindrical outer mesh, and a cylindrical dielectric separating the inner and outer meshes.

8. The air treatment device of claim 1 wherein the coil assembly is removably engageable with each insulating stand.

9. The air treatment device of claim 7 wherein a supply of voltage to the inner and outer meshes generates plasma which is discharged from the outer mesh.

10. The air treatment device of claim 1 wherein the insulating stand functions as a support platform to elevate the cylindrical coil above any surface on which the coil assembly is located wherein such a raised position of the cylindrical coil allows air circulation above and below the cylindrical coil whereby, by having the cylindrical coil raised, the inactivation zone extends circumferentially around the cylindrical coil and air can pass both above and below the coil assembly while being subjected to a uniform level of plasma.

11. The air treatment device of claim 10 wherein air flow is in a direction that is perpendicular to the orientation of the coil assembly, ensuring air exposure to the cylindrical coil is maximized.

12. The air treatment device of claim 7 wherein the cylindrical coil further comprises electrical contacts provided on the inner and outer meshes of the coil assembly and the electrical contacts comprise a first limb which is in the plane of the inner and outer meshes and a second limb which is perpendicular to the plane of the inner and outer meshes.

13. The air treatment device of claim 12 wherein the or each insulating stand is provided with a slot adapted to receive the second limb of the electrical contacts whereby in use, when the second limb of the electrical contacts is inserted into the slot in the or each insulating stand, the electrical contact is configured for connection to a power source so as to supply power to the inner and outer meshes when the coil assembly is located in the insulating stands.

14. The air treatment device of claim 1 wherein the plasma generator is configured to operate at a power density less than 1 W/cm$^2$ to operably generate a plasma discharge circumferentially about a longitudinal axis of the coil assembly.

15. The air treatment device of claim 14 wherein the coil assembly is operated at a power density in the range from 0.1 to 0.5 W/cm$^2$.

16. The air treatment device of claim 1 wherein the means for directing the charged airborne particles generated by the electrostatic precipitator into the inactivation zone comprises a voltage applied between the electrostatic precipitator and the plasma generator such that the air treatment device is adapted to generate charged airborne particles and at the same time, to direct the generated charged particles, by attracting said charged airborne particles towards the plasma generator, into the inactivation zone so as to expose the charged airborne particles to plasma in the inactivation zone.

17. The air treatment device of claim 1 wherein the voltage applied between the electrostatic precipitator and the plasma generator is in the range of between 1,000 and 10,000 volts.

18. The air treatment device of claim 1 wherein the plasma generator is positioned in proximity to but at a pre-determined distance from the electrostatic precipitator such that arcing is avoided while at the same time, allowing cooperation between the plasma generator and the electrostatic precipitator.

19. The air treatment device of claim 18 wherein the pre-determined distance between the electrostatic precipitator and the plasma generator is a distance in the range of from 0.5 cm to 2 cm.

20. A conduit comprising the air treatment device as claimed in claim 1.

21. An air treatment device comprising:
an arcuate electrostatic wire electrode configured to charge airborne particles in the vicinity of the electrode; and
a cylindrical coil assembly positioned adjacent to the arcuate wire electrode, the coil assembly configured to attract the charged airborne particles thereto and to discharge plasma;
wherein the arcuate electrode and the cylindrical coil assembly are concentric to each other.

22. An air treatment device comprising:
a linear array of needle electrodes configured to charge airborne particles in the vicinity of the electrode; and
a coil assembly positioned adjacent to the array of linear electrodes, the coil assembly configured to attract the charged airborne particles thereto and to discharge plasma.

23. The air treatment device of claim 22 wherein the voltage between the needle electrode array and the coil assembly is in the range of between 1,000 and 10,000 volts.

24. The air treatment device of claim 22 wherein the coil assembly is positioned in proximity to but at a pre-determined distance from the linear array of needle electrodes such that arcing is avoided while at the same time, enabling cooperation between the coil assembly and the needle electrodes so as to charge the airborne particles in the vicinity of the electrode and at the same time, attract the charged airborne particles towards the coil assembly.

25. The air treatment device of claim 24 wherein the pre-determined distance between the needle electrodes and the coil assembly is a distance in the range of from 0.5 cm to 2 cm.

26. The air treatment device of claim 22 further comprising a plasma generator and an insulating stand adapted for engaging with the plasma generator wherein the insulating stand functions as a support platform to elevate the plasma generator above any surface on which the plasma generator is located wherein such a raised position of the plasma generator allows air circulation above and below the plasma generator whereby, by having the plasma generator raised, an inactivation zone extends around the plasma generator and air can pass both above and below the plasma generator while being subjected to a uniform level of plasma.

27. The air treatment device of claim 26 wherein the air flows in a direction that is perpendicular to the orientation of the plasma generator ensuring air exposure to the plasma generator is maximized.

28. The air treatment device of claim 26 wherein the plasma generator comprises a coil assembly comprising an inner mesh electrode and an outer mesh electrode and comprising electrical contacts provided on the inner mesh and outer mesh of the coil assembly.

* * * * *